United States Patent
Xiao et al.

(10) Patent No.: US 12,390,353 B2
(45) Date of Patent: Aug. 19, 2025

(54) ENDOLUMINAL STENT AND ENDOLUMINAL STENT SYSTEM

(71) Applicant: Lifetech Scientific (Shenzhen) Co. Ltd., Guangdong (CN)

(72) Inventors: Benhao Xiao, Shenzhen (CN); Xuan Wu, Shenzhen (CN)

(73) Assignee: Lifetech Scientific (Shenzhen) Co. Ltd., Shenzhen (CN)

( * ) Notice: Subject to any disclaimer, the term of this patent is extended or adjusted under 35 U.S.C. 154(b) by 0 days.

(21) Appl. No.: 18/222,270

(22) Filed: Jul. 14, 2023

(65) Prior Publication Data
US 2023/0355415 A1 Nov. 9, 2023

Related U.S. Application Data

(63) Continuation of application No. 17/621,626, filed on Dec. 21, 2021, now abandoned.

(51) Int. Cl.
*A61F 2/954* (2013.01)
*A61F 2/06* (2013.01)
(Continued)

(52) U.S. Cl.
CPC ............. *A61F 2/954* (2013.01); *A61F 2/89* (2013.01); *A61F 2/962* (2013.01); *A61F 2002/067* (2013.01); *A61F 2250/0096* (2013.01)

(58) Field of Classification Search
CPC .. A61F 2/954; A61F 2/89; A61F 2/962; A61F 2002/067; A61F 2250/0096
See application file for complete search history.

(56) References Cited

U.S. PATENT DOCUMENTS

| 8,951,223 B2 * | 2/2015 | McNamara | A61M 27/002 604/9 |
| 2002/0058986 A1 * | 5/2002 | Landau | A61F 2/91 623/1.13 |

(Continued)

*Primary Examiner* — Jing Rui Ou
(74) *Attorney, Agent, or Firm* — Raymond Sun

(57) ABSTRACT

The present invention relates to an endoluminal stent and an endoluminal stent system, with the endoluminal stent being delivered to a site at which it is to be implanted by means of a delivery device comprising a sheath for receiving the endoluminal stent. The endoluminal stent comprises a hollow tube body portion, a connection portion and a flange portion, wherein the tube body portion is connected to one end of the connection portion, the flange portion has a connection end and a suspended end opposite one another, with the connection end being connected to the other end of the connection portion in a turning connection, and the suspended end being suspended, the flange portion comprising a flange section bare wave ring made of an elastic material; the suspended end is located at a distal side of the connection end when the endoluminal stent is in a natural state; the suspended end is located at a proximal side of the connection end when the endoluminal stent is received in the sheath; and after the flange portion is released from the sheath, the flange portion automatically turns over, and the suspended end moves from the proximal side of the connection end to the distal side of the connection end. The endoluminal stent of the present invention can enhance the anchoring force thereof.

4 Claims, 13 Drawing Sheets

(51) Int. Cl.
*A61F 2/89* (2013.01)
*A61F 2/962* (2013.01)

(56) References Cited

U.S. PATENT DOCUMENTS

| | | | | |
|---|---|---|---|---|
| 2004/0093058 A1* | 5/2004 | Cottone | A61F 2/91 | 623/1.11 |
| 2010/0268316 A1* | 10/2010 | Brenneman | A61B 17/083 | 604/8 |
| 2012/0290062 A1* | 11/2012 | McNamara | A61F 2/2442 | 623/1.1 |
| 2014/0277390 A1* | 9/2014 | Ratz | A61F 2/2418 | 623/1.26 |
| 2014/0277427 A1* | 9/2014 | Ratz | A61F 2/2409 | 623/2.38 |
| 2017/0049590 A1* | 2/2017 | Hingston | B29C 33/485 | |

* cited by examiner

ENDOLUMINAL STENT AND ENDOLUMINAL STENT SYSTEM

FIELD

The present invention relates to the field of interventional medical devices, and more particularly, relates to an endoluminal stent and an endoluminal stent system.

BACKGROUND

At present, the reconstruction of a blood flow transport channel is assisted by a single endoluminal stent or a plurality of endoluminal stents to isolate the impact of blood flow on an arterial dissection or aneurysm.

If a branch blood vessel extends out of a diseased area, usually at least two vascular stents are used together. As shown in FIG. 1, an arterial dissection 12 is located at an aortic arch 11 and extends to the vicinity of a left subclavian artery 13. A vascular stent 30 may be implanted in the aortic arch 11 first, and then a side hole 33a is formed on a side of the vascular stent 30. The side hole 33a is aligned with a proximal opening of the left subclavian artery 13. A branch endoluminal stent 50a is implanted in the left subclavian artery 13. The branch endoluminal stent 50a moves easily under the scouring of blood flow, leading to internal leakage. As shown in FIG. 2, the branch endoluminal stent 50a in the prior art is a branch endoluminal stent with a rim 52a. The branch endoluminal stent 50a that resembles a top hat is also called a top hat stent, and includes a tube body 51a and the rim 52a surrounding an end opening of the tube body 51a. The rim 52a is connected to the tube body 51a by means of a membrane, and the rim 52a is substantially perpendicular to the tube body 51a. When a blood transport channel between the aortic arch 11 and the left subclavian artery 13 is established, the rim 52a is expected to abut an inner wall of the main stent 30 to achieve the purpose of preventing internal leakage. Although the rim 52a can be close to the inner wall of the main stent 30, the branch endoluminal stent 50a does not generate a force causing the rim 52a to abut against the inner wall of the main stent 30. Therefore, it is difficult to fit the rim 52a with the inner wall of the main stent 30, and the anchoring force between the branch endoluminal stent 50a and the main stent 30 is poor, which allows the branch endoluminal stent 50a to fall off.

SUMMARY

In view of the above, it is necessary to provide an endoluminal stent to solve the problem of the poor anchoring force of the branch endoluminal stent in the prior art.

One of the embodiments provides an endoluminal stent, with the endoluminal stent being delivered to a site at which it is to be implanted by means of a delivery device including a sheath for receiving the endoluminal stent; the endoluminal stent including a hollow tube body portion, a connection portion and a flange portion, wherein the tube body portion is connected to one end of the connection portion, the flange portion has a connection end and a suspended end opposite one another, with the connection end being connected to the other end of the connection portion in a turning connection, and the suspended end being suspended, and the flange portion includes a flange section bare wave ring made of an elastic material; the suspended end is located at a distal side of the connection end when the endoluminal stent is in a natural state; the suspended end is located at a proximal side of the connection end when the endoluminal stent is received in the sheath; and after the flange portion is released from the sheath, the flange portion automatically turns over, and the suspended end moves from the proximal side of the connection end to the distal side of the connection end.

In one of the embodiments, the tube body portion includes a tube body section membrane, the connection portion includes a connection section membrane, with the connection section membrane being connected to the tube body section membrane, the flange portion further includes a flange section membrane, with the flange section membrane being arranged on the flange section bare wave ring, and the flange section membrane being connected to the connection section membrane, and the flange section bare wave ring is connected to the connection section membrane in a turning connection by means of the flange section membrane.

In one of the embodiments, the connection portion further includes a connection section bare wave ring, with the connection section bare wave ring being made of an elastic material, the connection section membrane is arranged on the connection section bare wave ring, and the flange section bare wave ring is connected to the connection section bare wave ring in a turning connection.

In one of the embodiments, the flange section bare wave ring includes a crest away from the connection portion, the flange section membrane includes a first end and a second end, with the first end being connected to the connection section membrane, and the second end being opposite to the first end, and an interval is formed between the second end and the crest.

In one of the embodiments, the range of the interval between the second end and the crest is 0.5 mm≤D≤3 mm.

In one of the embodiments, when the endoluminal stent is in the natural state, the angle between the flange portion and an axial direction of an outer surface of the tube body portion ranges from greater than 0 to less than or equal to 80°.

In one of the embodiments, when the endoluminal stent is in the natural state, the length of the flange portion is less than or equal to the vertical distance from the suspended end of the flange portion to the outer surface of the tube body portion.

In one of the embodiments, the endoluminal stent further includes an imaging structure, with the imaging structure being arranged on a wave rod of the flange section bare wave ring, and the imaging structure extending along the longitudinal direction of the wave rod of the flange section bare wave ring.

In one of the embodiments, the extending length of the imaging structure is at least ⅓ of the length of the wave rod of the flange section bare wave ring.

One of the embodiments provides an endoluminal stent system that includes a delivery device and the above-mentioned endoluminal stent, wherein the delivery device includes a sheath, with the sheath being formed with a receiving lumen for receiving an endoluminal stent.

The above-mentioned endoluminal stent is used together with a main stent, the endoluminal stent is delivered to an inner lumen of the main stent via a side hole of the main stent by means of the sheath, and the endoluminal stent is gradually released from its proximal end to its distal end; when the flange portion is received in the sheath, the suspended end of the flange portion is located at the proximal side of the connection end. Because the flange portion includes the flange section bare wave ring that is made of an elastic material, and the connection end is connected to one end of the connection portion in a turning connection, after the flange portion is completely released, the flange section bare wave ring can generate a turning force, which causes the flange portion to automatically turn toward the distal end of the endoluminal stent, and then causes the suspended end to move to the proximal side of the connection end. After the flange portion is completely released, the sheath is pulled to drive the flange portion to approach the side hole, the flange portion can be hung on an inner wall near the side hole of the main stent, and the turning force generated by the flange section bare wave ring forces the flange portion to adhere to the inner wall of the main stent; and after the flange portion is adhered to the inner wall of the main stent, the remaining portions of the endoluminal stent are released, and the flange portion is hung on the inner wall of the main stent under the effect of the turning force, which can prevent the endoluminal stent from moving after being scoured by blood flow, thereby increasing the anchoring force of the endoluminal stent.

DETAILED DESCRIPTION OF THE EMBODIMENTS

Figure 1:
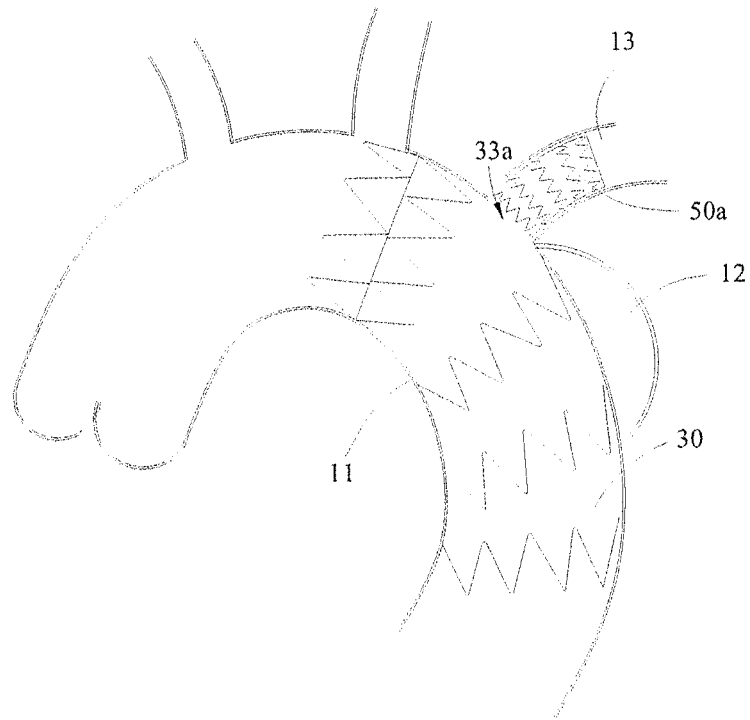
FIG. 1 is a schematic structural diagram showing the cooperation of a branch endoluminal stent and a main stent in the prior art.
Figure 2:
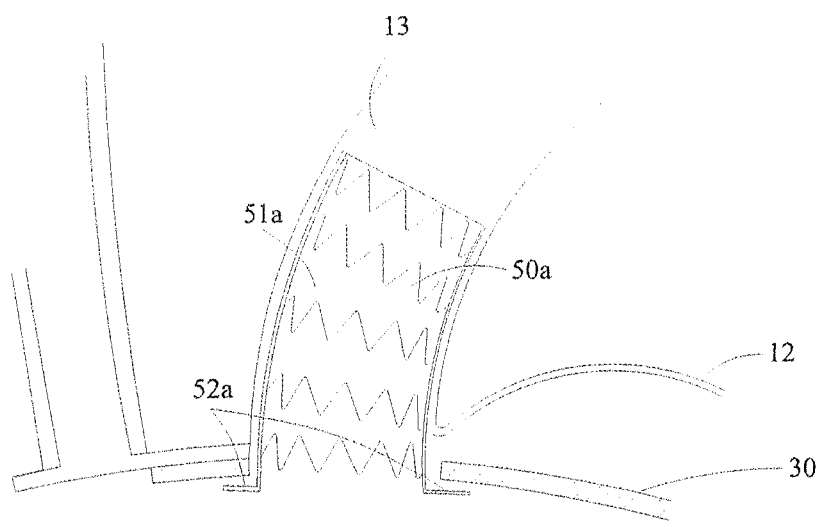
FIG. 2 is a schematic structural diagram showing the cooperation of a branch endoluminal stent and a main stent in the prior art.

In order to make the above objects, features and advantages of the present invention clearer and easier to understand, specific embodiments of the present invention will be described in detail below in conjunction with the accompanying drawings. In the following description, numerous specific details are illustrated for full understanding of the present invention. However, the present invention can be implemented by other means different from those described herein, a person skilled in the art may make similar improvements without departing from the essence of the present invention, and therefore, the present invention is not limited to the specific embodiments disclosed below.

It should be noted that when one element is "fixed" or "arranged" on another element, the element may be directly located on the other element or a medium element may exist. When one element is considered to be "connected" to another element, the element may be directly connected to the other element or a medium element may exist simultaneously. The terms "vertical", "horizontal", "left", "right" and the like used herein are for illustrative purposes only, and are not meant to be the only embodiments.

Unless otherwise defined, all technical and scientific terms used herein have the same meanings as commonly understood by those of ordinary skill in the technical field of the present invention. The terms used in the description of the present invention are only for the purpose of describing specific embodiments, but are not intended to limit the present invention. The term "and/or" used herein includes any and combinations of one or more relevant items listed.

For the convenience of description, a lumen is illustrated in terms of a blood vessel, and the blood vessel may be an aortic arch, or a thoracic aorta, or an abdominal aorta. It should be appreciated by a person of ordinary skill in the art that the blood vessel is described by way of example only and does not limit the present invention. The solutions of the present invention are applicable to various human lumens, for example, a digestive tract lumen. Various modifications and variations taught by the present invention are all within the scope of the present invention. Additionally, in the description of the blood vessel, the orientation may be defined in terms of a direction of blood flow, and it is defined in the present invention that blood flows from a proximal end to a distal end.

In order to facilitate the understanding of the technical solutions of the present invention, "turning connection" and "automatic turning" are described as follows.

Turning connection indicates that an inner side of a ring or cylindrical structure (the ring or cylindrical structure is made of an elastic material) is first turned outwardly and then connected to another structure (such as a tube). An outward turning angle ranges from greater than 90° to less than or equal to 180°. Outward turning refers to turning the inner side of the ring or cylindrical structure outwardly. When the outward turning angle is 180°, the original inner side and the original outer side can be interchanged; that is, the original inner side becomes an outer side after turning outwardly, and the original outer side becomes an inner side after turning outwardly.

The following explains the principle that the ring or cylindrical structure can achieve automatic turning.

Figure 3:
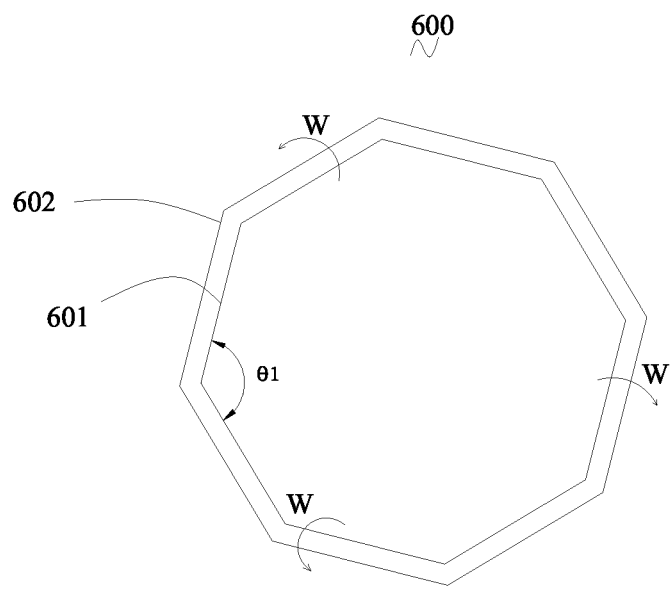
FIG. 3 is a schematic structural diagram of a regular octagonal ring structure in a natural state.

As shown in FIG. 3, a regular octagonal ring structure 600 is taken as an example for description. The ring structure 600 is made of an elastic material. For the ring structure 600 made of an elastic material, the ring structure 600 includes an inner side 601 and an outer side 602, and the ring structure 600 has an internal angle θ1 in an original state (that is, in a natural state). Taking one end (an axial end) of the ring structure 600 as a fulcrum, a torque is applied to the other end of the ring structure 600, so that the ring structure 600 turns outwardly in a W direction, and the range of the outward turning angle is greater than 0°, and less than equal to 180°.

Figure 4:
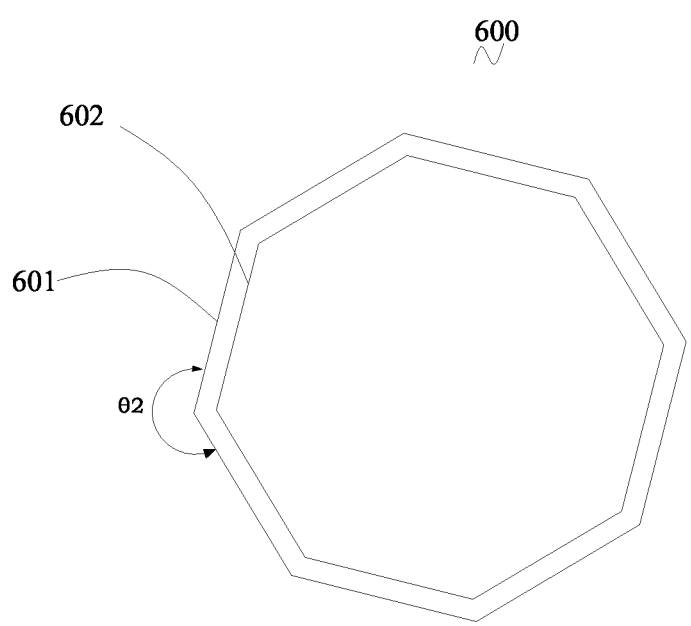
FIG. 4 is a schematic structural diagram of the regular octagonal ring structure after turning over.

As shown in FIG. 4, when the outward turning angle is 180°, the original inner side 601 and the original outer side 602 can be interchanged. In other words, the inner side 601 in the original state (that is, before turning outwardly) becomes an outer side after turning outwardly, the outer side 602 in the original state (that is, before turning outwardly) becomes an inner side after turning outwardly. At this time, the internal angle θ1 in the original state becomes an external angle θ2 after turning outwardly. In essence, the ring structure 600 turns outwardly because of elastic deformation. The elastically deformed ring structure 600 is in an unstable state. If the torque acting on the ring structure is removed, the ring structure 600 will turn inwardly (that is, deform in a reverse manner along the original deformation path) back to the original state with the outwardly turning fulcrum as a fulcrum, at this time, θ2 becomes θ1 again. The ring structure 600 in the original state does not deform elastically, which is a stable state.

Figure 5:
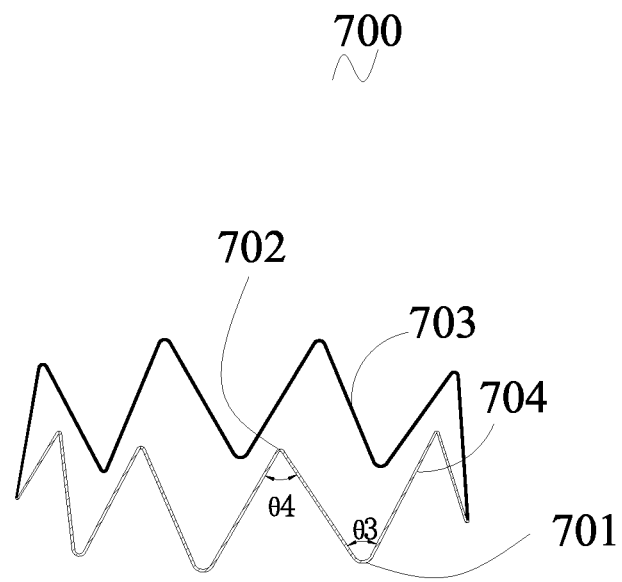
FIG. 5 is a schematic structural diagram of an M-shaped wave ring in a natural state.
Figure 6:
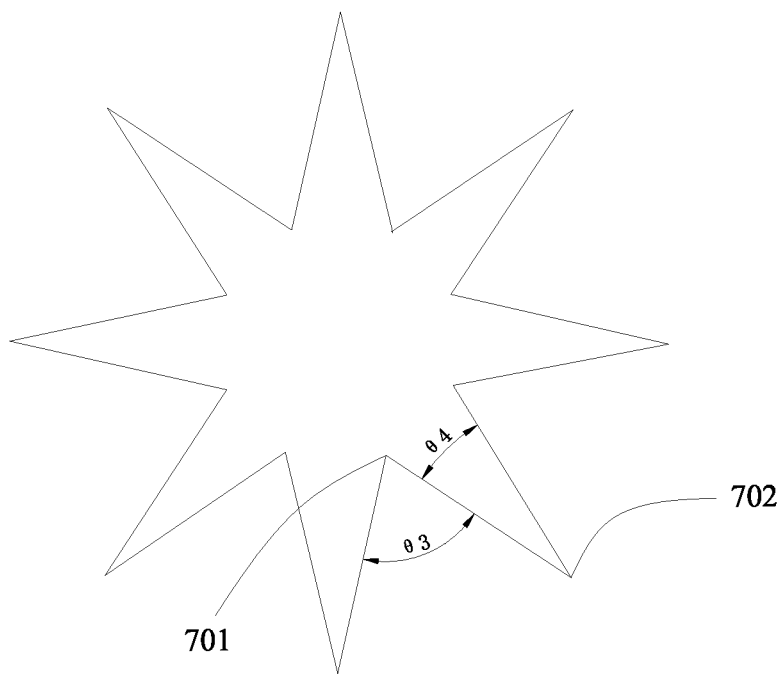
FIG. 6 is a schematic structural diagram of the M-shaped wave ring after turning over.

M-shaped or Z-shaped wave rings commonly used in a vascular stent also constitute a closed ring structure because they are made of an elastic material. Taking the M-shaped wave ring as an example, the M-shaped wave ring can also automatically turn over after turning outwardly. As shown in FIG. 5, the M-shaped wave ring 700 includes a trough 701 and a crest 702, and the M-shaped wave ring 700 has an inner side 703 and an outer side 704. In the original state (natural state), the M-shaped wave ring 700 has an angle θ3 at the trough 701 and an angle θ4 at the crest 702. The M-shaped wave ring 700 turns outwardly under the effect of a torque, and the M-shaped wave ring 700, after turning outwardly, has a tendency to deform and return to the original state. As shown in FIG. 6, when the M-shaped wave ring 700 turns outwardly, a torque is applied to the M-shaped wave ring 700. One end of the trough 701 of the M-shaped wave ring 700 serves as a fulcrum, and the crest 702 of the M-shaped wave ring 700 turns toward one side, so that the M-shaped wave ring 700 turns outwardly. In this process, when the M-shaped wave ring 700 turns outwardly within a range of that is greater than or equal to 0° and less than or equal to 90°, θ3 will become smaller and θ4 will not change. The change in θ3 will cause the M-shaped wave ring 700 to generate a resisting moment against the outward turning, thereby resisting the outward turning of the M-shaped wave ring 700 due to the torque. If the torque acting on the M-shaped wave ring 700 is removed at this time, the resisting moment of the M-shaped wave ring 700 will drive the M-shaped wave ring 700 to turn inwardly (that is, automatically turn back and return to the original state). In addition, when the outward turning angle of the M-shaped wave ring 700 is just 90°, the angle θ3 at the trough 701 is the smallest (that is, the deformation of the angle θ3 at the trough 701 is the largest, and the elastic force generated by the deformation of the angle is the largest), and the resisting moment has the greatest hindrance to the outward turning. In other words, when the angle of outward turning is greater than 0° and less than or equal to 90°, if the torque is removed, the M-shaped wave ring 700 can automatically deform, that is, the M-shaped wave ring 700 can automatically turn over.

Figure 7:
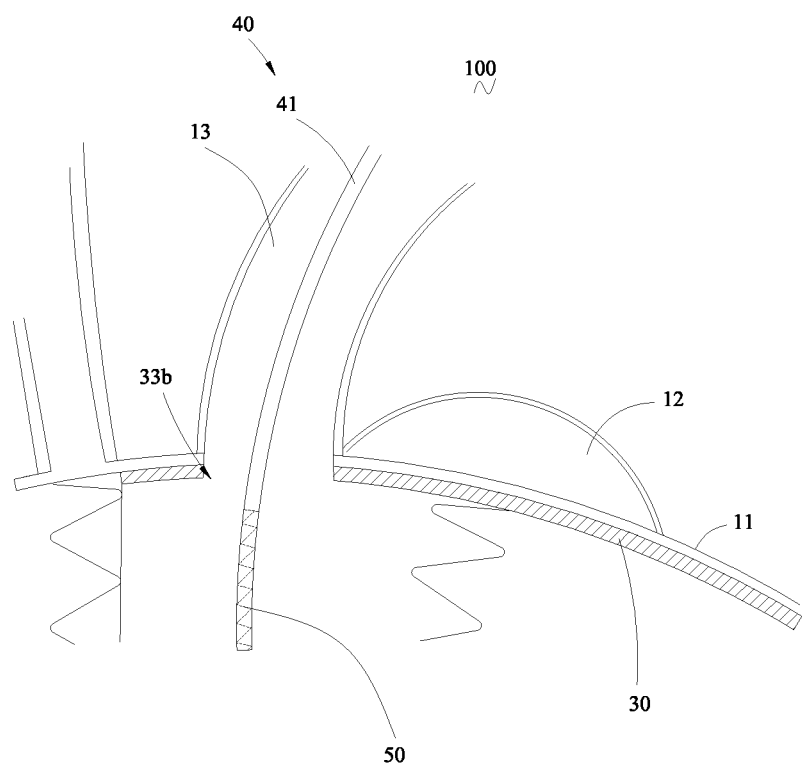
FIG. 7 is a diagram showing the implantation process of an endoluminal stent in an embodiment of the preset invention.

As shown in FIG. 7, an endoluminal stent system 100 provided in an embodiment of the present invention includes a delivery device 40 and an endoluminal stent 50. The endoluminal stent 50 is delivered to a site at which the endoluminal stent 50 is to be implanted (for example, into a left subclavian artery 13) by means of the delivery device 40.

The delivery device 40 includes a sheath 41, with the sheath 41 being formed with a receiving lumen for receiving the endoluminal stent 50.

Figure 8:
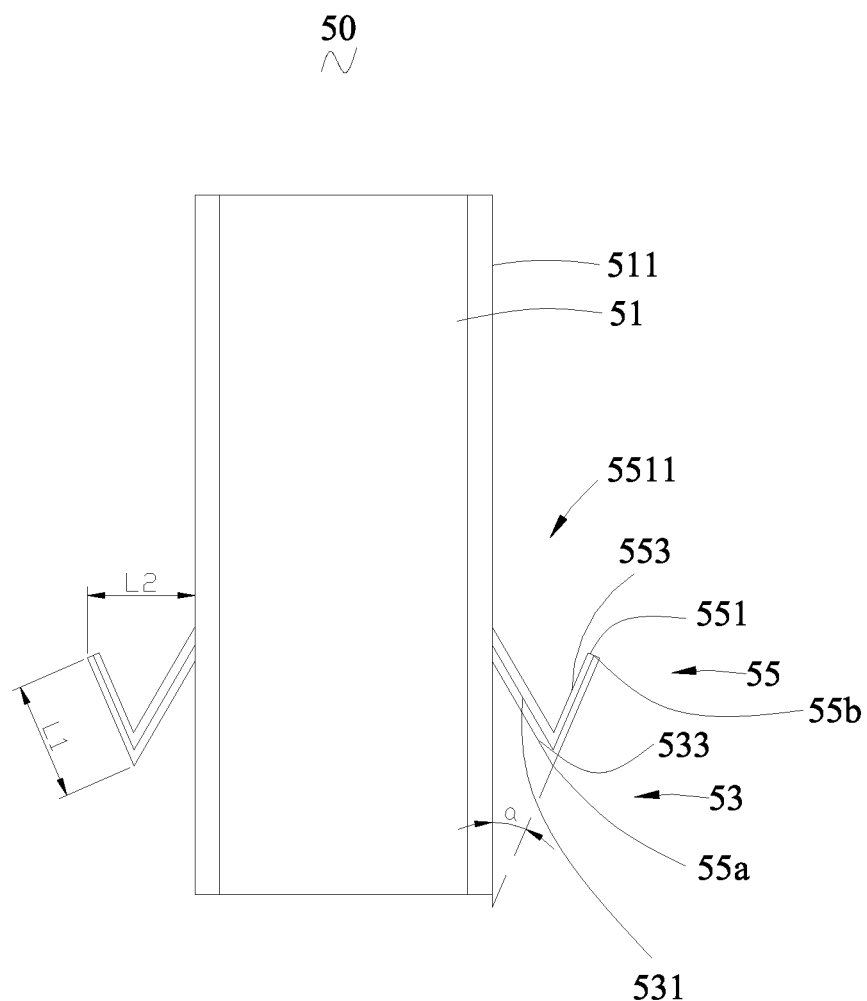
FIG. 8 is a schematic structural diagram of the endoluminal stent in a natural state according to one embodiment of the present invention.

As shown in FIG. 8, the endoluminal stent 50 includes a hollow tube body portion 51, a connection portion 53 and a flange portion 55.

The tube body portion 51 includes a tube body section bare stent (not shown in the figure) and a tube body section membrane 511. The tube body section bare stent includes a plurality of tube body section bare wave rings (not shown) arranged axially, and the tube body section bare wave rings are made of a metal elastic material. When loaded into the receiving lumen of the sheath 41, the endoluminal stent 50 may radially deform, so that the endoluminal stent 50 can be loaded into the sheath 41 and expanded in a blood vessel. The tube body section membrane 511 is a PTFE membrane or a PET membrane, and the tube body section membrane 511 is arranged on the tube body section bare wave rings to isolate blood flow.

The connection portion 53 is connected to a portion between two ends of the tube body portion 51, and the connection portion 53 includes a connection section bare wave ring 531 and a connection section membrane 533. The connection section bare wave ring 531 is made of an elastic metal material, and the connection section bare wave ring 531 may be shaped as an M-shaped wave, a Z-shaped wave, or waves of other shapes. The connection section membrane 533 is a PTFE membrane or a PET membrane, the connection section membrane 533 is arranged on the connection section bare wave ring 531, and one end of the connection section membrane 533 is connected to the tube body section membrane 511. Specifically, the connection section membrane 533 may be connected to a portion between two ends (that is, a proximal end and a distal end) of the tube body section membrane 511.

The flange portion 55 has a connection end 55a and a suspended end 55b opposite one another, with the connection end 55a being connected to one end of the connection portion 53 in a turning connection, and the suspended end 55b being suspended to form an opening 5511. Specifically, the flange portion 55 includes a flange section bare wave ring 551 and a flange section membrane 553, with the flange section membrane 553 being arranged on the flange section bare wave ring 551.

The flange section bare wave ring 551 is made of an elastic metal material, and the flange section bare wave ring 551 may be shaped as an M-shaped wave, a Z-shaped wave, or waves of other shapes. Since the flange section bare wave ring 551 is made of an elastic metal material, and the flange section bare wave ring 551 is of a closed ring structure, the flange section bare wave ring 551 can be connected with another structure after turning outwardly (that is, the flange section bare wave ring 551 can be connected with another structure in a turning connection). One end of the flange section bare wave ring 551 is connected to the connection section bare wave ring 531 in a turning connection. Understandably, the connection end 55a is formed by the end that is connected to the connection section bare wave ring 531 in a turning connection of the flange section bare wave ring 551 and the flange section membrane 553 arranged on this end. The suspended end 55b is formed by the other end of the flange section bare wave ring 551 and the flange section membrane 553 arranged on the other end.

The flange section membrane 553 is a PTFE membrane or a PET membrane, and the flange section membrane 553 is connected to the connection section membrane 533, so that the flange section bare wave ring 551 can be connected to the tube body portion 51 in a turning connection by means of the connection section membrane 533, and the flange section bare wave ring 551 can also be connected to the tube body portion 51 in a turning connection by means of the connection section bare wave ring 531. In other words, the flange portion 55 can be connected to the tube body portion 51 in a turning connection by means of the connection portion 53.

Figure 9:
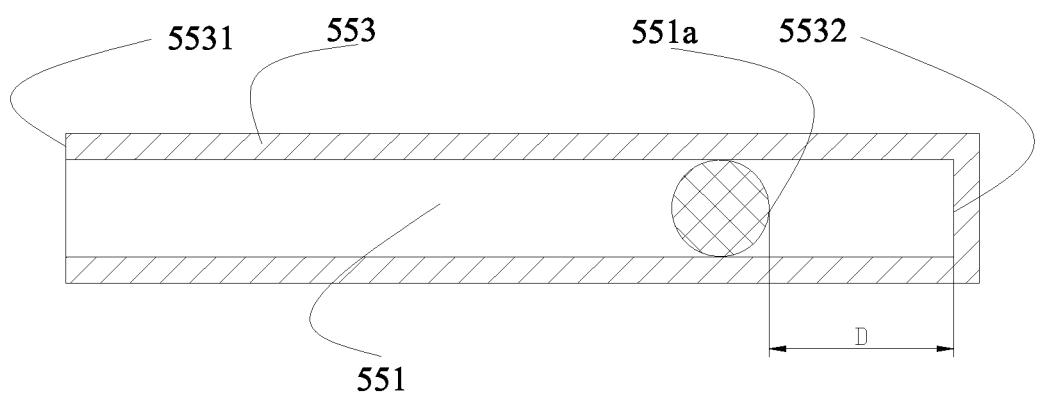
FIG. 9 is a schematic structural diagram of a flange portion according to one embodiment of the present invention.

As shown in FIG. 9, the flange section bare wave ring 551 includes a crest 551a away from the connection portion 53, the flange section bare wave ring 551 further includes a trough (not shown) near the connection portion 53; the flange section membrane 553 includes a first end 5531 and a second end 5532, with the first end 5531 being connected to the connection section membrane 533, and the second end 5532 being opposite to the first end 5531; and an interval D is formed between the second end 5532 and the crest 551a. A range of the interval D between the second end 5532 and the crest 551a is: 0.5 mm≤D≤3 mm, where mm is a millimeter unit.

When the endoluminal stent 50 is in a natural state, the suspended end 55b is located at a distal side of the connection end 55a, a diameter of the flange portion 55 is gradually decreased from its suspended end 55b to its connection end 55a, an angle between the flange portion 55 and the connection portion 53 is an acute angle, and the range of an angle a between the flange portion 55 and an axial direction of an outer surface of the tube body portion 51 is greater than 0 and less than or equal to 80°. The axial direction refers to a direction parallel to a central axis of the tube body portion 51 and pointing to the distal end of the tube body portion 51 along its proximal end. Because the angle a between the flange portion 55 and the axial direction of the outer surface of the tube body portion 51 is smaller, the turning force is stronger and the fitting effect is better. Preferably, when the endoluminal stent 50 is in the natural state, the range of the angle a between the flange portion 55 and the axial direction of the outer surface of the tube body portion 51 is between 0-30°. When the endoluminal stent 50 is received in the sheath 41, the suspended end 55b is located at a proximal side of the connection end 55a.

Of course, in other embodiments, the flange portion 55 may include only the flange section bare wave ring 551, and one end of the flange section bare wave ring 551 is connected to the connection portion 53. Alternatively, the connection portion 53 may include only the connection section membrane 533, and the flange section bare wave ring 551 after turning outwardly can be connected to the connection section membrane 533 be means of sutures, or connected to the connection section membrane 533 by means of the flange section membrane 553, thereby achieving the turning connection between the flange portion 55 and the connection portion 53.

When the endoluminal stent 50 is in the natural state, the length L1 of the flange portion 55 is less than or equal to the distance L2 from the suspended end 55b (that is, the end formed with the opening 5511 of the flange portion 55) to the outer surface of the tube body portion 51. Thus, the connection portion 53 in a radially compressed state easily drives the flange section 55 to turn, which increases the turning speed of the flange section 55 and saves operation time. Of course, the tube body portion 51 may be of a straight tube structure or a non-straight tube structure. When the tube body portion 51 has a non-straight tube structure, a portion where the tube body portion 51 contacts the connection portion 53 is the contact portion. The distance L2 from the suspended end 55b to the outer surface of the tube body portion 51 refers to the radial distance between the suspended end 55b and the contact portion, and the radial direction refers to a diameter direction of the tube body portion 51.

Figure 10:
FIG. 10 is a diagram showing the compressed state of the endoluminal stent according to one embodiment of the present invention.

As shown in FIG. 10, before the endoluminal stent 50 is received in the sheath 41, the flange portion 55 and the connection portion 53 turn toward the proximal end of the endoluminal stent 50 under an external force, and the suspended end 55b is located at the proximal side of the connection end 55a of the flange portion 55. Then the flange portion 55 and the connection portion 53 are compressed, so that the flange portion 55 and the connection portion 53 are attached to the outer surface of the radially compressed tube portion 51, and the endoluminal stent 50 is received in the sheath 41. At this time, the suspended end 55b received in the sheath 41 is located at the proximal side of the connection end 55a.

After the flange portion 55 is released from the sheath 41, the suspended end 55b of the flange portion 55 is expanded under the effect of a radial expansion force of the flange section bare wave ring 551, the connection end 55a of the flange portion 55 is connected to the connection portion 53, and the connection portion 53 is received in the sheath 41, so that the sheath 41 radially compresses the connection end 55a by means of the connection portion 53. The suspended end 55b is subjected to the radial expansion force, the connection end 55a is subjected to the radial compression, the connection end 55a is connected to the connection portion 53 in a turning connection to form a fulcrum, and the flange portion 55 will turn over to be roughly perpendicular to a central axis of the sheath 41 with the connection end 55a as the fulcrum, that is, the angle of outward turning of the flange section bare wave ring 551 is within a range of greater than 0° and less than or equal to 90°. In other words, the flange section bare wave ring 551 satisfies the condition of automatic turning, and the flange portion 55 can automatically turn over by means of the turning force generated by the flange section bare wave ring 551, so that the suspended end 55b is caused to turn toward the distal end, and the suspended end 55b can move to the distal side of the connection end 55a.

Figure 11:
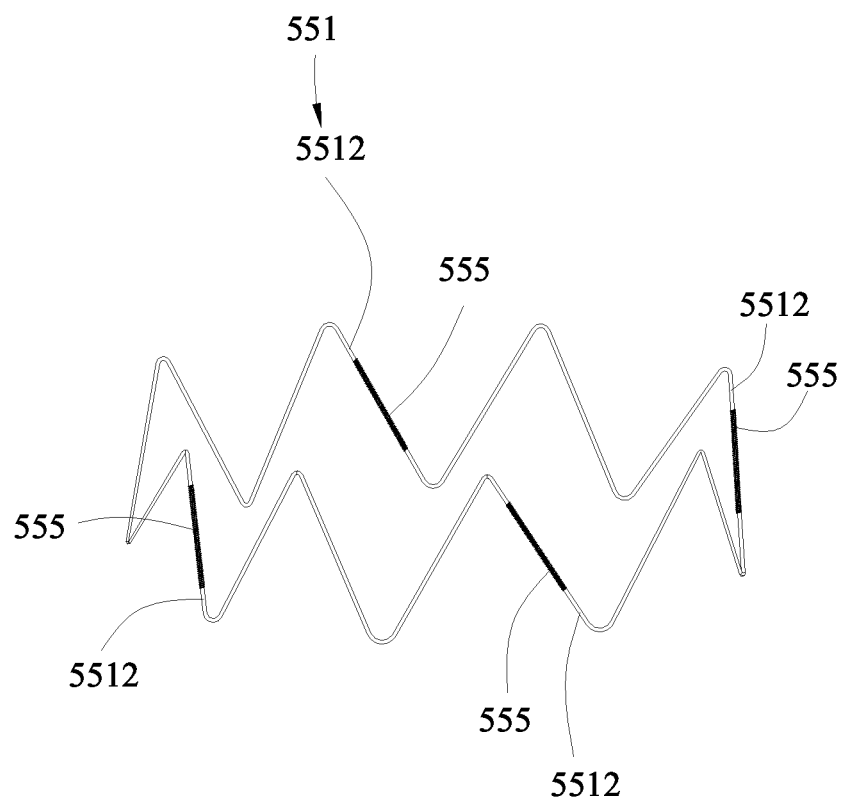
FIG. 11 is a schematic structural diagram of a flange section bare wave ring and an imaging structure according to one embodiment of the present invention.

As shown in FIG. 11, the endoluminal stent 50 further includes an imaging structure 555. The imaging structure 555 is made of an imaging material (such as a tantalum wire), the imaging structure 555 is arranged on a wave rod 5512 of the flange section bare wave ring 551, and the imaging structure 555 extends along a length direction of the wave rod 5512. For example, the imaging structure 555 is arranged on the wave rod 5512 of the flange section bare wave ring 551 by means of spiral winding or welding. The imaging structure 555 spirally extends on the wave rod 5512, so that an image of the imaging structure 555 under DSA is elongated. During the automatic turning of the flange portion 55, the imaging structure 555 turns together with the flange portion 55, and the elongated imaging structure 555 facilitates the display of the automatic turning process of the flange portion 55 by means of its image. Of course, in other embodiments, the imaging structure 555 may also be arranged on the flange section membrane 553. The imaging structure 555 may be a non-circular, such as a triangular, quadrangular, or a non-spherical imaging structure 555.

The number of the imaging structures 555 is four, and the four imaging structures 555 are distributed at equal intervals along a circumferential direction of the flange portion 55. The four imaging structures 555 facilitate the imaging of an overall contour of the flange portion 55. In other embodiments, the number of the imaging structures 555 may be 1, 2, 3, 5, or another number. The more imaging structures 555 are provided, the higher the imaging precision of the complete contour of the flange portion 55.

In order to ensure that the imaging structure 555 can be imaged normally under DSA, the extending length of the imaging structure 555 is at least ⅓ of the length of the wave rod 5512. The imaging material of each imaging structure 555 may be continuous or discontinuous. In order to improve the imaging performance, preferably, the imaging material of each imaging structure 555 is continuous.

Figure 12:
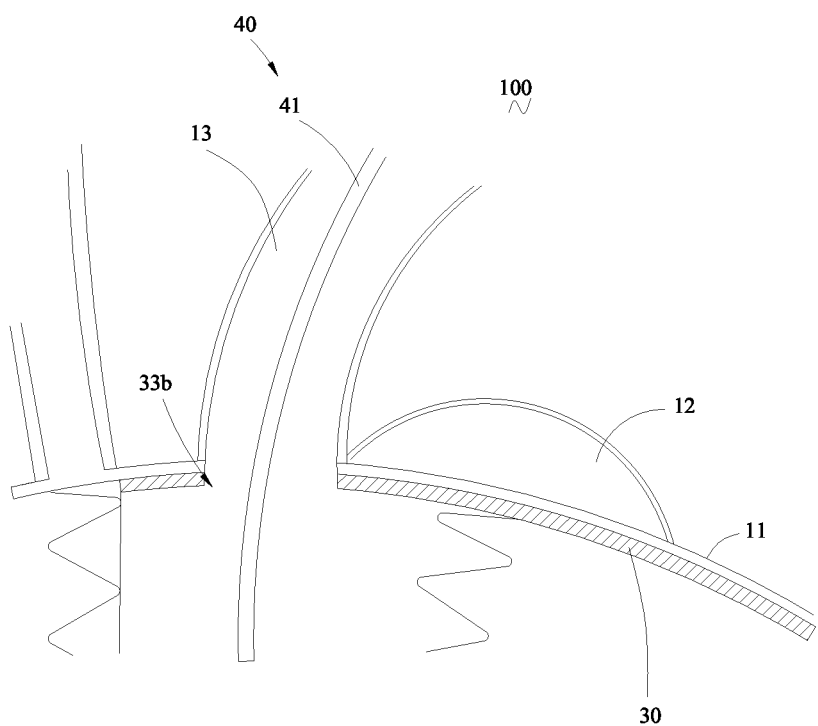
FIG. 12 is a first implantation process diagram of an endoluminal stent according to an embodiment of the present invention.

As shown in FIG. 12, the endoluminal stent 50 in this embodiment can be used together with a main stent 30, and can be implanted in a diseased area from where a branch blood vessel extends. Specifically, the main stent 30 is implanted in a main lumen (for example, implanted in an aortic arch 11). After the main stent 30 is implanted in the aortic arch 11, a side hole 33b is formed in the main stent 30. The side hole 33b of the main stent 30 is aligned with an opening of a branch lumen (for example, a left subclavian artery 13) extending from the main lumen.

A portion of the sheath 41 that is preloaded with the endoluminal stent 50 is delivered from the left subclavian artery 13 to a lumen of the main stent 30 along the left subclavian artery 13 via the side hole 33b of the main stent 30; that is, from a distal end of the left subclavian artery 13 to a proximal end of the left subclavian artery 13. At this time, the endoluminal stent 50 is radially compressed in the receiving lumen of the sheath 41.

Figure 13:
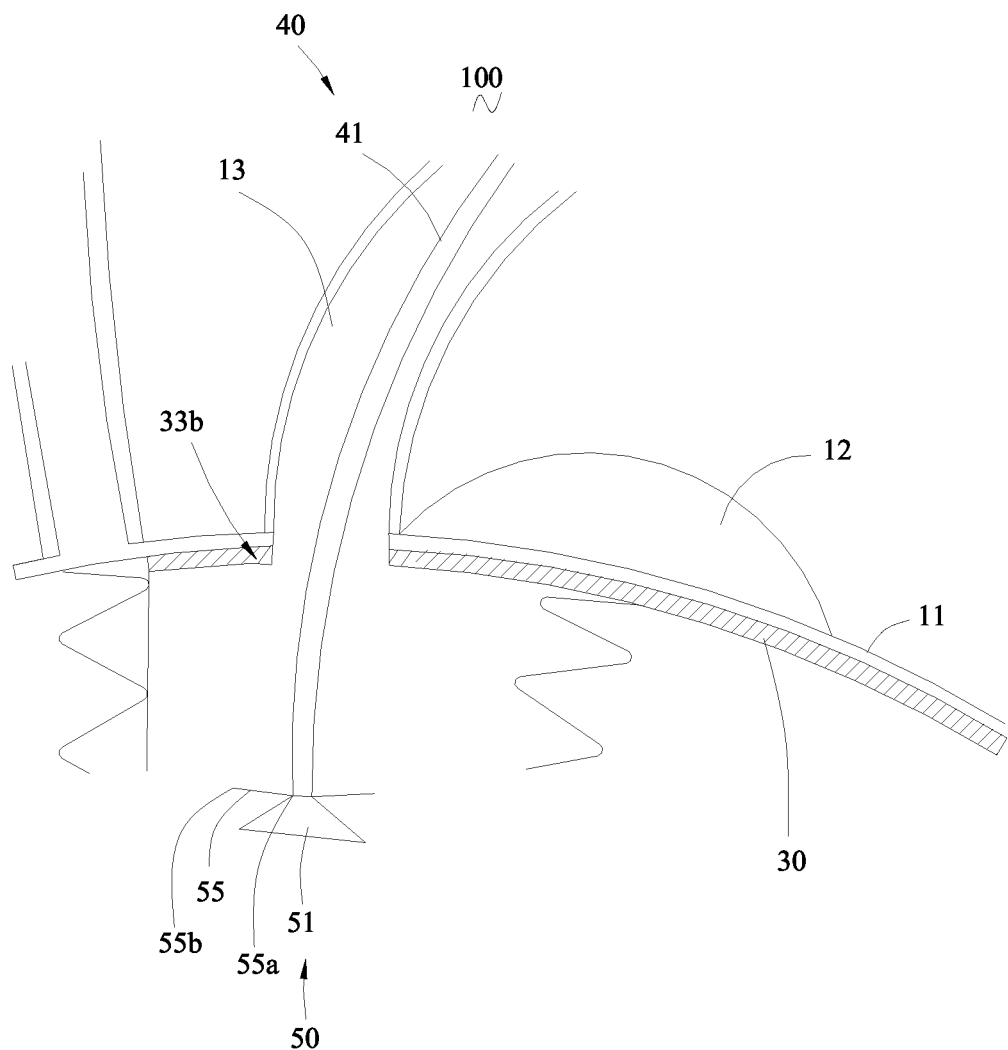
FIG. 13 is a second implantation process diagram of an endoluminal stent according to an embodiment of the present invention.
Figure 14:
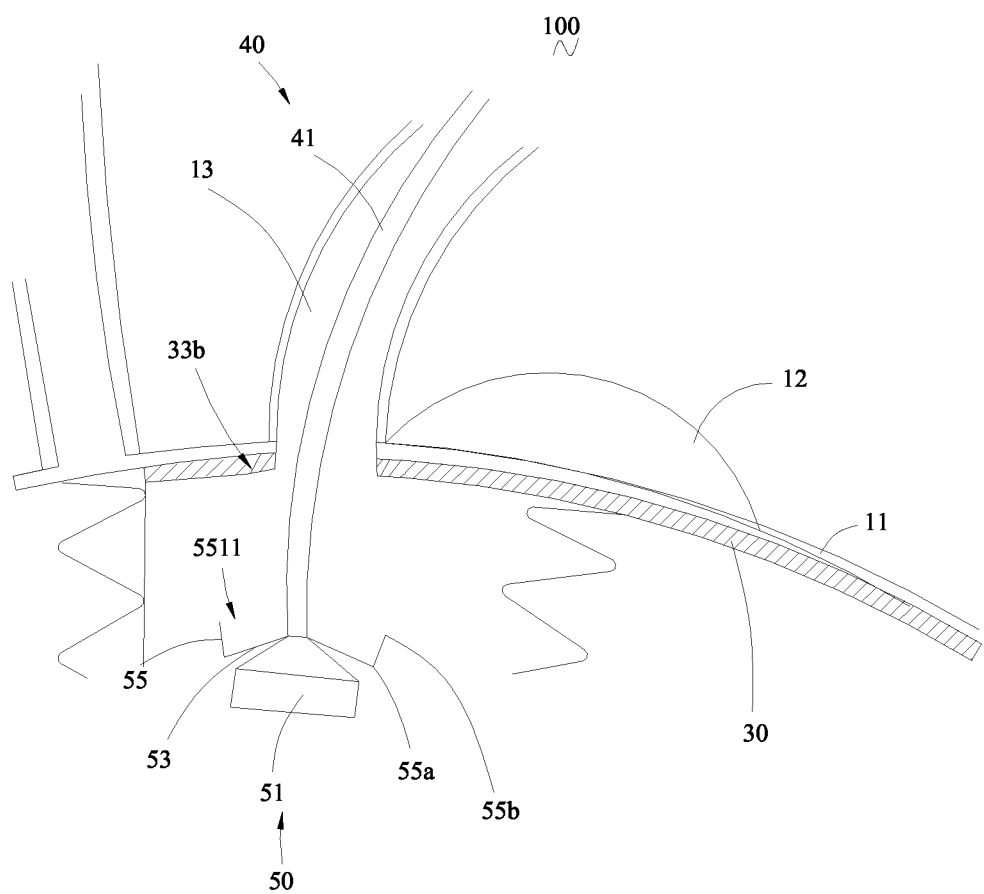
FIG. 14 is a third implantation process diagram of an endoluminal stent according to an embodiment of the present invention.

As shown in FIG. 13, the sheath 41 is removed in a direction opposite to the delivery direction (that is, along a direction of blood flow), the endoluminal stent 50 is gradually released from its proximal end to its distal end until the flange portion 55 is completely released, and the flange portion 55 turns over to be perpendicular to the central axis of the sheath 41 under the combined action of the flange section bare wave ring 551 and the sheath 41, so that the flange portion 55 achieves automatic turning. As shown in FIG. 14, the sheath 41 continues to be withdrawn, the suspended end 55b of the flange portion 55 turns toward the distal end of the endoluminal stent 50, and the suspended end 55b moves to the distal side of the connection end 55a. At this time, the opening 5511 of the flange portion 55 faces the distal end of the tube body portion 51, and the diameter of the flange portion 55 is gradually decreased from its suspended end 55b to its connection end 55a. A portion of the tube body portion 51 that is released in the lumen of the main stent 300 can also be restored to the shape in the natural state by means of self-expansion of its tube body section bare stent. At this time, the diameter of the released portion of the tube body portion 51 is approximately the same as the diameter of the left subclavian artery 13, the diameter of the suspended end 55b is greater than the diameter of the left subclavian artery 13, and the diameter of the suspended end 55b is greater than the diameter of the side hole 33b of the main stent 30.

Figure 15:
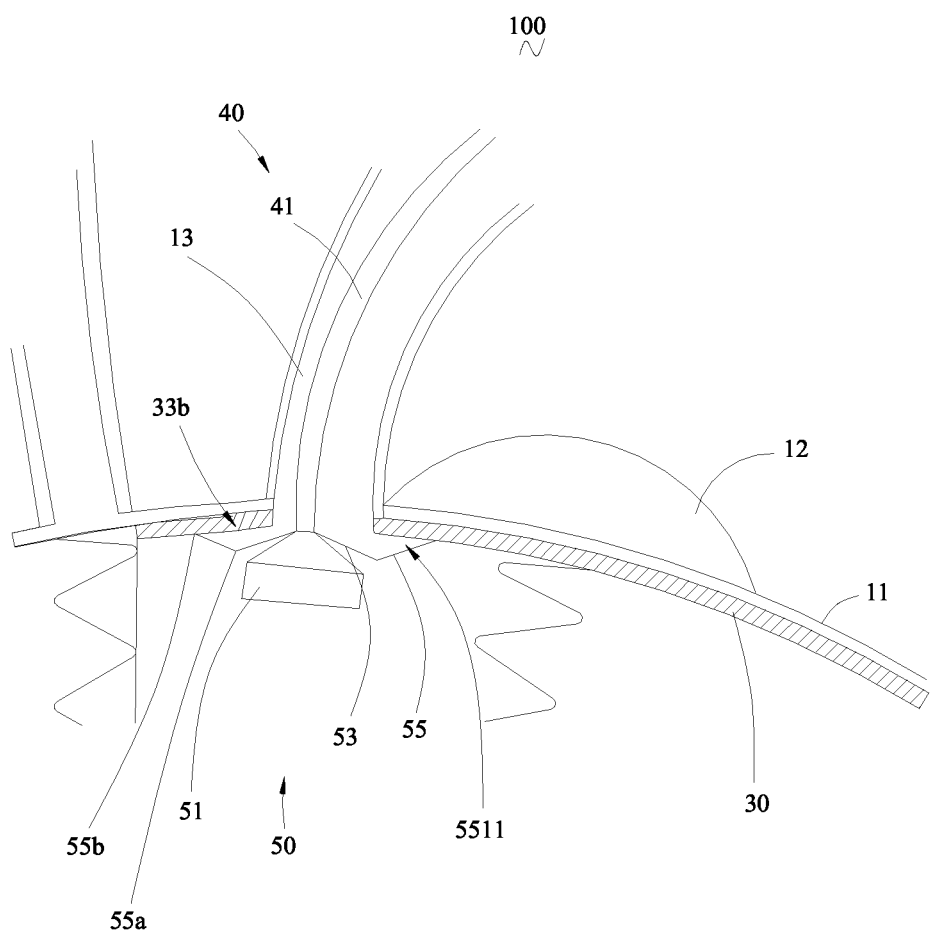
FIG. 15 is a fourth implantation process diagram of an endoluminal stent according to an embodiment of the present invention.
Figure 16:
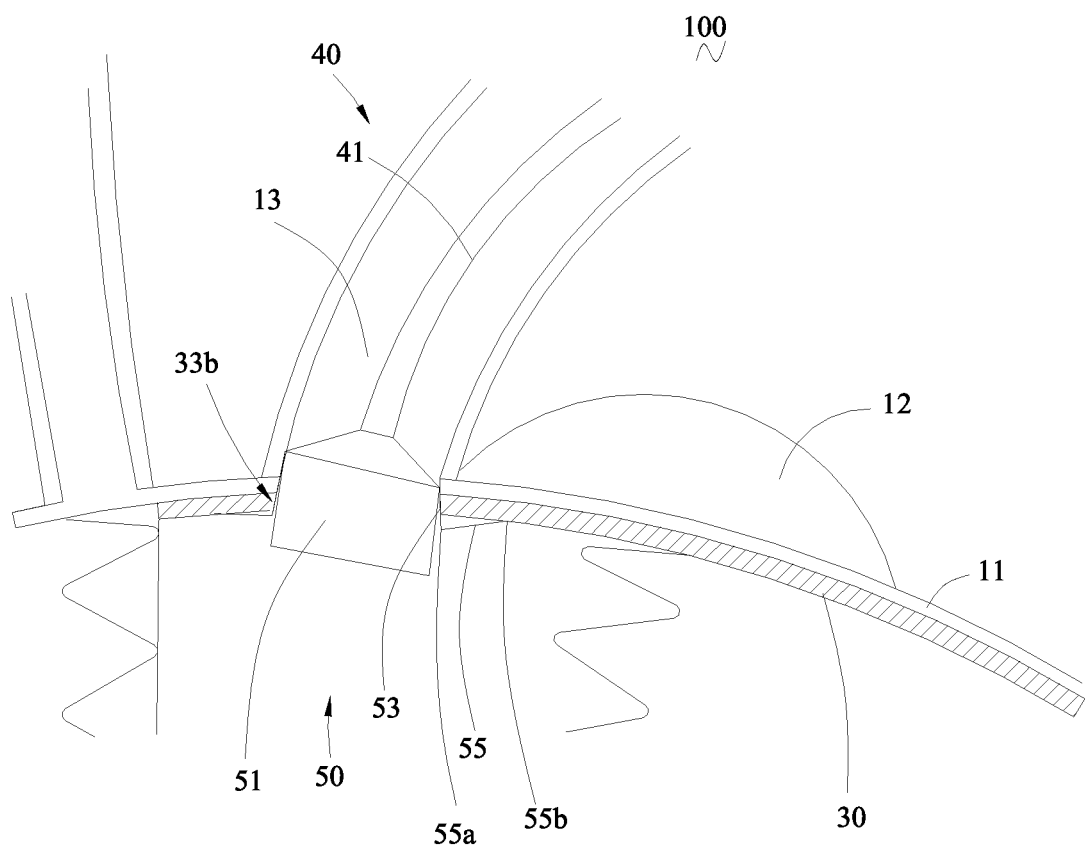
FIG. 16 is a fifth implantation process diagram of an endoluminal stent according to an embodiment of the present invention.

After the flange portion 55 and the connection portion 53 are completely released, the sheath 41 is pulled in the direction opposite to the delivery direction, so that the endoluminal stent 50 moves synchronously with the sheath 41. As shown in FIG. 15, the suspended end 55b is hung on an inner wall of the main stent 30 near the side hole 33b. As shown in FIG. 16, the sheath 41 continues to be pulled, and the flange portion 55 turns toward the proximal end of the endoluminal stent 50 under the extrusion of the inner wall of the main stent 30 until the flange portion 55 adheres to the inner wall of the main stent 30. The sheath 41 can be pulled appropriately again, so that the flange portion 55 adheres more closely to the inner wall of the main stent 30. Other portions of the endoluminal stent 50 are then gradually released. During the turning of the flange section 55, the flange section membrane 553 shrinks in a direction close to the connection section 53. At this time, the crest 551a easily pierces the flange section membrane 553 in contact with it. The interval D between the second end 5532 and the crest 551a provides a space for the shrinkage of the flange section membrane 553. Even after the flange section membrane 553 shrinks, the crest 551a and the flange section membrane 553 still reserve an interval or just abut against each other, which can prevent the crest 551a from piercing the flange section membrane 553. The range of the interval D is: $0.5\ mm \leq D \leq 3\ mm$, which can prevent the crest 551a from piercing the flange section membrane 553 and can also avoid wasting the membrane.

When the release of the endoluminal stent 50 from its proximal end to distal end is completed, the distal end of the tube body portion 51 is implanted in the left subclavian artery 13, and the branch endoluminal stent 50 is stably anchored in the left subclavian artery 13 by means of the radial expansion capability of the tube body section bare stent. The connection portion 53 and the tube body portion 51 are together radially compressed by the left subclavian artery 13, the flange portion 55 is kept in an outward turning state under the joint restriction of the connection section and the inner wall of the main stent 30, and the flange portion 55 maintains an automatic back turning force in this state, that is, the suspended end 55b of the flange portion 55 maintains a tendency to turn toward the distal end of the endoluminal stent 50. Therefore, the endoluminal stent 50 can firmly adhere to the inner wall of the main stent 30. Because the flange portion 55 maintains the turning force for continuing to turn toward the distal end of the endoluminal stent 50, the flange portion 55 provides better pre-tightening force, the endoluminal stent 50 is anchored in the left subclavian artery 13 more stably, and the endoluminal stent 50 cannot be easily pulled out of the branch when the sheath 41 is pulled.

Since the flange portion 55 further includes the flange section membrane 553, and the flange portion 55 maintains the automatic turning force, the flange section membrane 553 closely adheres to the inner wall of the main stent 30, which prevents internal leakage (type III internal leakage) at the junction of the endoluminal stent 50 and the main stent 30.

For the endoluminal stent 50, the more closely the flange portion 55 adheres to the main stent 30, the more leak-proof it is. The main stent 30 adopts fenestration in vivo, and its fenestration position is unknown in advance, so any imaging material cannot be placed at the fenestration position. As a result, the position of the side hole 33b of the main stent 30 cannot be accurately determined during operation, and thus the flange portion 55 cannot be accurately positioned. Therefore, during implantation, if the release effect of the endoluminal stent 50 can be accurately implemented, that is, if the adhesion of the flange portion 55 to the inner wall of the main stent 30 can be implemented, the success rate of the operation will be greatly improved.

The flange portion 55 of the endoluminal stent 50 returns to the natural state after being completely released. The sheath 41 is pulled, so that the endoluminal stent 50 moves synchronously with the sheath 41. The flange portion 55 returning to the natural state abuts against the inner wall of the main stent 30. The flange portion 55 gradually adheres to the inner wall of the main stent 30 during the pulling. In this process, the image of the imaging structure 555 arranged on the flange portion 55 can be viewed by means of DAS. By viewing the image of the imaging structure 555, the position of the inner wall of the main stent 30 can be determined very accurately, and whether the flange portion 55 adheres to the inner wall of the main stent 30 can also be accurately determined, so that the release of the endoluminal stent 50 can be adjusted at any time, which can accurately accomplish the accurate positioning of the endoluminal stent 50.

Figure 17:
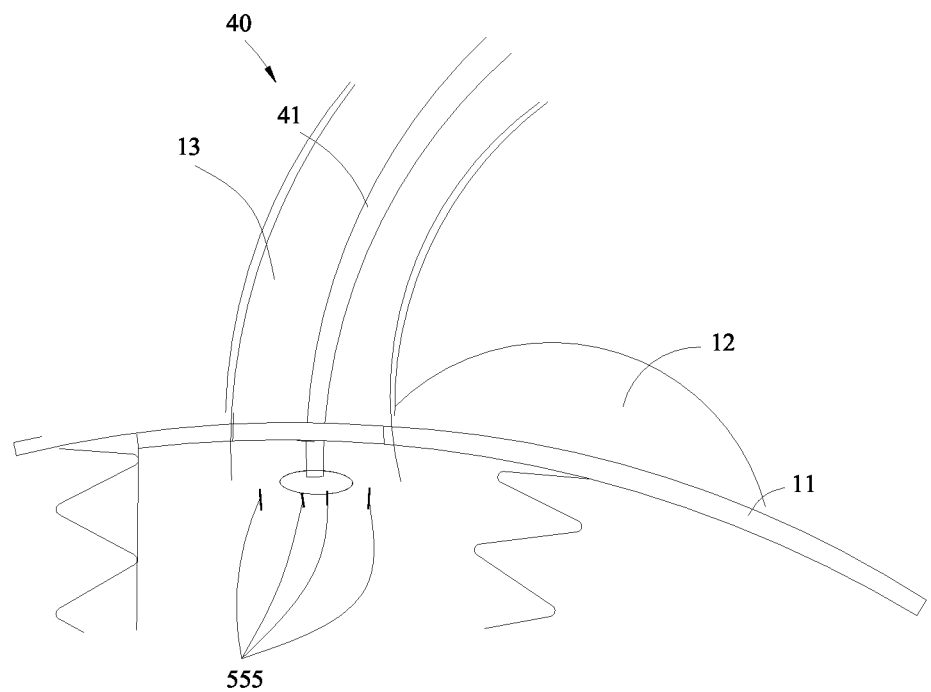
FIG. 17 is an imaging state diagram of the endoluminal stent during implantation according to an embodiment of the present invention.
Figure 18:
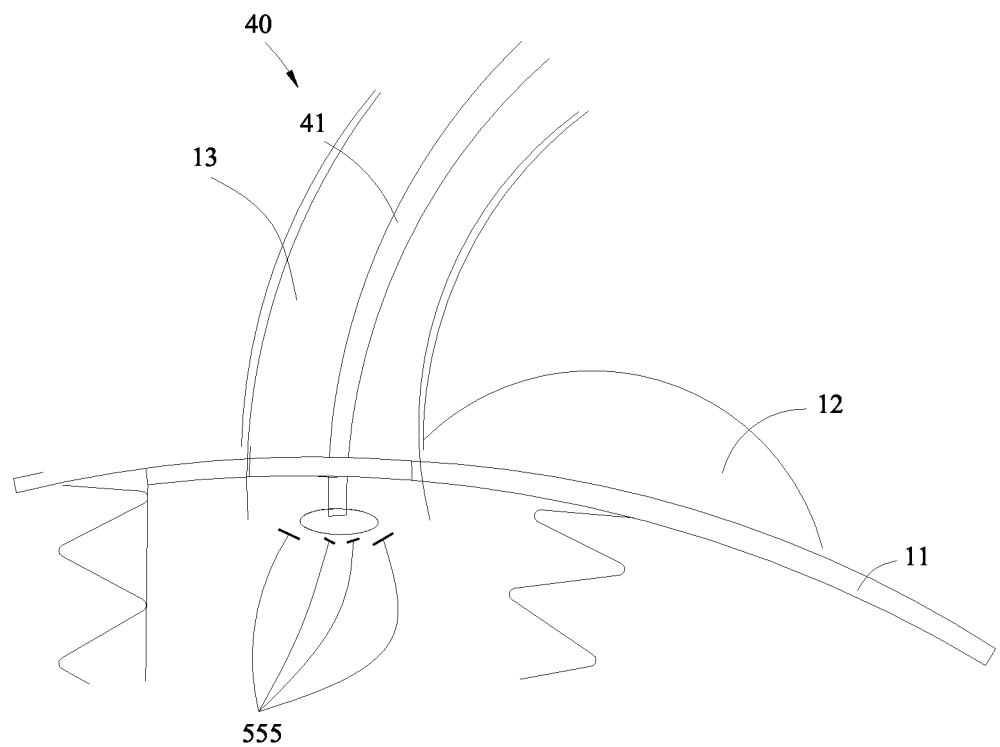
FIG. 18 is another imaging state diagram of the endoluminal stent during implantation according to an embodiment of the present invention.
Figure 19:
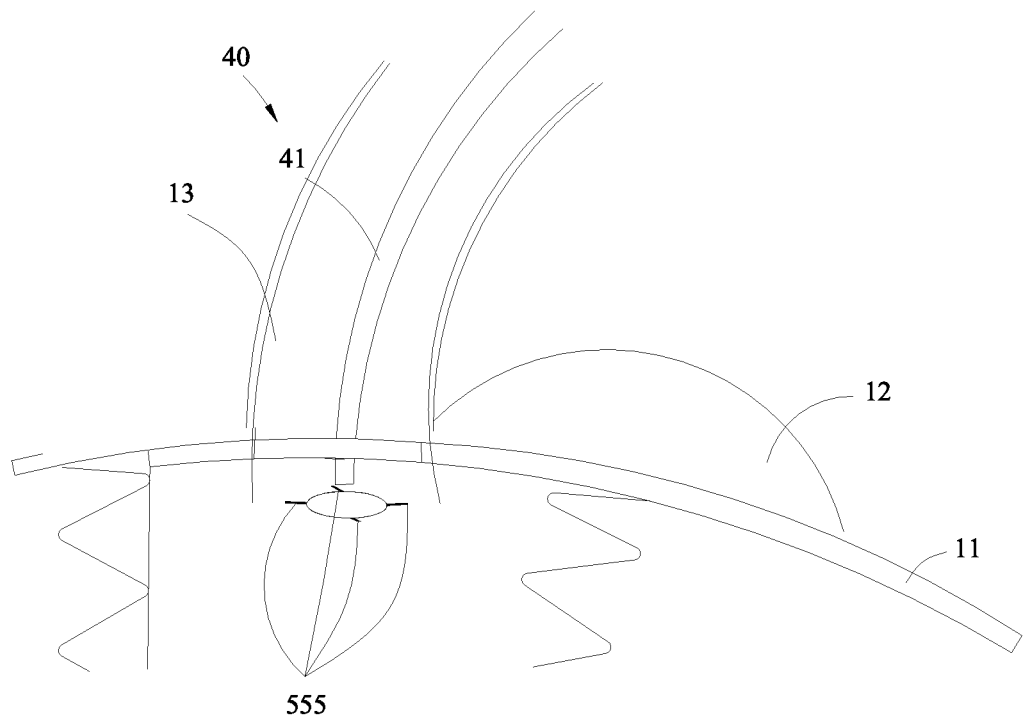
FIG. 19 is still another imaging state diagram of the endoluminal stent during implantation according to an embodiment of the present invention.

Specifically, as shown in FIG. 17, after the flange portion 55 and the connection portion 53 are released from the sheath 41, the four elongated imaging structures 555 arranged on the flange portion 55 can be viewed under DSA. The imaging structures 555 are approximately parallel to the central axis of the sheath 41. The overall contour of the flange portion 55 can be roughly determined by means of the four imaging structures 555. The sheath 41 is pulled to drive the endoluminal stent 50 to move synchronously, and it can be seen that the four elongated imaging structures 555 move in parallel without rotating. The sheath 41 continues to be pulled, and as shown in FIG. 18, it can be seen that the four imaging structures 555 start to roll toward the proximal end of the endoluminal stent 50, and at this time, it can be determined that the flange portion 55 has been hung on the inner wall of the main stent 30. As shown in FIG. 19, the sheath 41 continues to be pulled again, the imaging structures 555 continue to turn over until they are substantially perpendicular to the central axis of the sheath 41, and at this time, it can be determined that the flange portion 55 completely adheres to the inner wall of the main stent 30.

Figure 20:
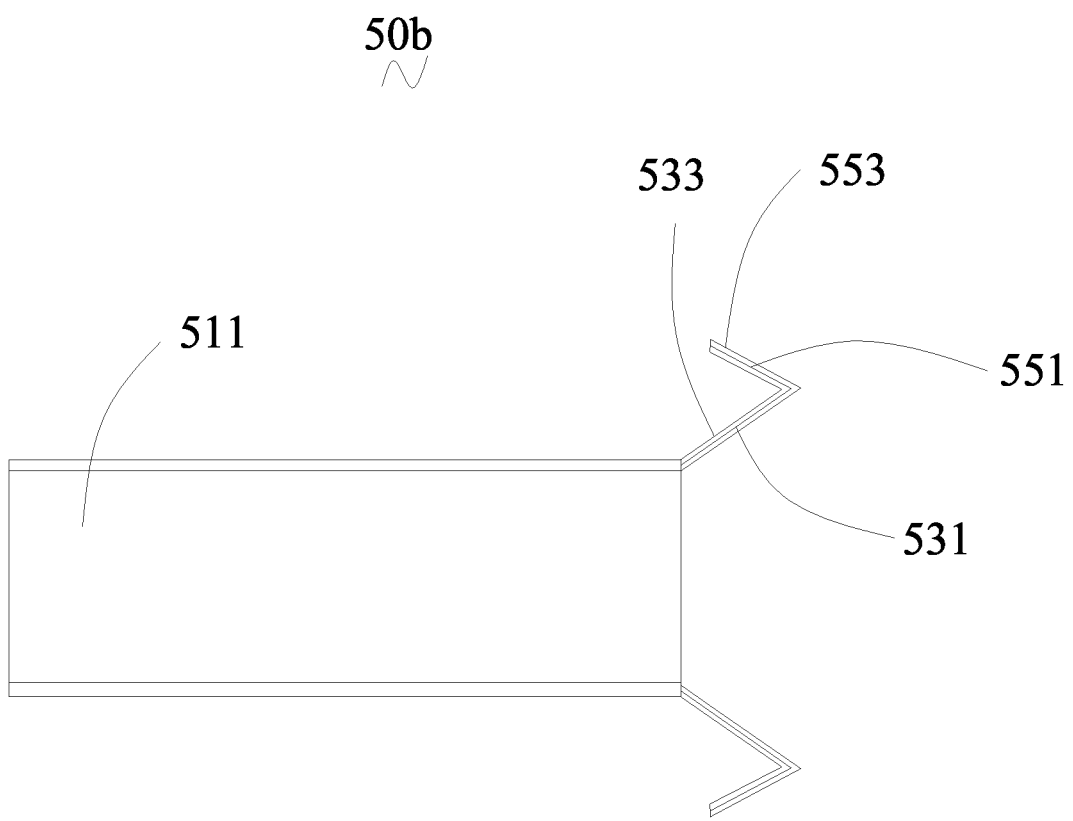
FIG. 20 is a schematic structural diagram of the endoluminal stent in a natural state according to an embodiment of the present invention.

As shown in FIG. 20, an endoluminal stent 50b provided in another embodiment has substantially the same structure as the above-mentioned endoluminal stent 50, except for the following. The connection portion 53 is connected to the proximal end of the tube body portion 51. Specifically, the connection portion 53 may be connected to the proximal end of the tube body section membrane 511 by means of the connection section membrane 533. The connection section bare wave ring 531 is connected to the tube body section membrane 511 by means of the connection section membrane 533. By taking the end of the connection section membrane 533 that is connected to the tube body section membrane 511 as a fulcrum, the connection portion 53 can swing to the proximal end of the endoluminal stent 50 or the distal end of the endoluminal stent 50 under the effect of an external force.

The technical features of the above-described embodiments can be combined arbitrarily. For the purpose of simplicity in description, all the possible combinations of the technical features in the above embodiments are not described. However, as long as the combinations of these technical features do not have contradictions, they shall fall within the scope of the specification.

The foregoing embodiments only describe several implementation modes of the present invention, and their descriptions are specific and detailed, but cannot therefore be understood as limitations to the patent scope of the present invention. It should be noted that a person of ordinary skill in the art could also make many alterations and improvements without departing from the spirit of the present invention, and these alterations and improvements shall all fall within the protection scope of the present invention. Therefore, the patent protection scope of the present invention should be subject to the appended claims.

The invention claimed is:

1. An endoluminal stent, with the endoluminal stent configured to be delivered to a site at which the endoluminal stent is to be implanted by means of a delivery device comprising a sheath for receiving the endoluminal stent, wherein the endoluminal stent comprises a hollow tube body portion, a connection portion and a flange portion, the tube body portion having a proximal end and a distal end; wherein one end of the connection portion is connected to the tube body portion at a location between the proximal end and the distal end, the flange portion has a connection end and a suspended end opposite one another, with the connection end being connected to another end of the connection portion in a turnable connection, and the suspended end being suspended; wherein the connection portion extends towards the proximal end of the tube body portion; wherein the flange portion comprises a flange section bare wave ring made of an elastic material; the suspended end is located at a distal side of the connection end when the endoluminal stent is in a natural state;

the suspended end is located at a proximal side of the connection end when the endoluminal stent is received in the sheath; and after the flange portion is released from the sheath, the flange portion automatically turns over, and the suspended end moves from the proximal side of the connection end to the distal side of the connection end in a manner such that the flange portion extends towards the distal end of the tube body portion, and the connection portion and the flange portion extend in opposite directions; and wherein the tube body portion comprises a tube body section membrane, the connection portion comprises a connection section membrane, with the connection section membrane being connected to the tube body section membrane, the flange portion further comprises a flange section membrane, with the flange section membrane being arranged on the flange section bare wave ring and the flange section membrane being connected to the connection section membrane, and the flange section bare wave ring is connected to the connection section membrane in the turning connection by means of the flange section membrane.

2. The endoluminal stent of claim 1, wherein the connection portion further comprises a connection section bare wave ring, the connection section bare wave ring being made of an elastic material, the connection section membrane is arranged on the connection section bare wave ring, and the flange section bare wave ring is connected to the connection section bare wave ring in the turning connection.

3. The endoluminal stent of claim 1, wherein the flange section bare wave ring comprises a crest away from the connection portion, the flange section membrane comprises a first end and a second end, with the first end being connected to the connection section membrane, and the second end being opposite to the first end, and an interval is formed between the second end and the crest.

4. The endoluminal stent of claim 3, wherein a range of the interval between the second end and the crest is $0.5 \text{ mm} \leq D \leq 3 \text{ mm}$.

* * * * *